(12) United States Patent
Bell et al.

(10) Patent No.: US 9,770,677 B2
(45) Date of Patent: Sep. 26, 2017

(54) FLUID OPTIMIZATION

(71) Applicant: Hil Tech LLC, Conroe, TX (US)

(72) Inventors: Kevin William Bell, Conroe, TX (US); James Dwight Andrews, Jr., Conroe, TX (US); Christopher Shannan Barnes, Conroe, TX (US)

(73) Assignee: HIL TECH LLC, Conroe, TX (US)

( * ) Notice: Subject to any disclaimer, the term of this patent is extended or adjusted under 35 U.S.C. 154(b) by 0 days.

(21) Appl. No.: 14/726,476

(22) Filed: May 30, 2015

(65) Prior Publication Data

US 2016/0346713 A1    Dec. 1, 2016

(51) Int. Cl.
| | |
|---|---|
| *B01D 17/12* | (2006.01) |
| *B01D 17/02* | (2006.01) |
| *G01N 9/32* | (2006.01) |
| *G01N 9/00* | (2006.01) |
| *E21B 21/08* | (2006.01) |
| *E21B 21/06* | (2006.01) |

(52) U.S. Cl.
CPC ......... *B01D 17/12* (2013.01); *B01D 17/0217* (2013.01); *E21B 21/065* (2013.01); *E21B 21/08* (2013.01); *G01N 9/002* (2013.01); *G01N 9/32* (2013.01); *G01N 2009/006* (2013.01)

(58) Field of Classification Search
None
See application file for complete search history.

(56) References Cited

U.S. PATENT DOCUMENTS

| | | | |
|---|---|---|---|
| 6,607,659 B2 * | 8/2003 | Hensley | E21B 21/065 175/206 |
| 7,540,837 B2 * | 6/2009 | Scott | E21B 21/062 494/10 |
| 2014/0357464 A1 * | 12/2014 | Stone | B04B 1/20 494/10 |

* cited by examiner

*Primary Examiner* — Terry Cecil
(74) *Attorney, Agent, or Firm* — Basil M. Angelo; Angelo Mikeska PLLC (57) ABSTRACT

A separation system including a control unit, a first pump connected to the control unit, and a first valve in fluid communication with the first pump and connected to the control unit. Also, a first density meter in fluid communication with the first valve and connected to the control unit. The system further includes a separator in fluid communication with the density meter and connected to the control unit and a tank in fluid communication with the separator. The system also includes a second pump in fluid communication with the tank and connected to the control unit, as well as a second density meter in fluid communication with the second pump and connected to the control unit and a second valve in fluid communication with the second density meter and connected to the control unit.

24 Claims, 10 Drawing Sheets

FLUID OPTIMIZATION

BACKGROUND OF THE INVENTION

In hydrocarbon drilling and production operations, different types of separation devices are used for separating a mixture of liquid phases of different densities from a solid phase. The separation of the liquid phases from the solid phase may be necessary or desirable in order to, for example, provide a liquid phase of a desired density and/or viscosity. The separation may also be necessary or desirable in order to provide a final product having properties that allow either the liquid phase or solid phase to be reusable in the drilling or production operation.

While different types of separation devices are used, typical separation devices operate through either the principle of cyclone or centrifuge separation. In cyclone separators, the flow is introduced into a chamber in a tangential manner at high energy, thereby inducing a rotating flow pattern within the chamber that causes lighter components to migrate toward the chamber axis while heavier components migrate toward the outside. In centrifuge separators, a mixture is introduced into a vessel that is rotatable about an axis. The vessel is then rotated at a desired speed, such that denser components of the mixture migrate to the outside while lighter components accumulate nearer the centrifuge axis. In certain centrifuges, the outer wall of the vessel is porous, so that liquid components may be extracted, thereby leaving solid material on the porous wall of the vessel.

During hydrocarbon drilling and production operations, fluids that are used in the operation are often recycled to reduce costs. As part of the recycling operation, fluids may be passed through a separator to remove solids allowing for reuse of a liquid phase. In such operations, the removal of the solid phase may also make the solid phase reusable in other aspects of the operation.

In order to provide a fluid of a desired density, during conventional operations, a drilling operator manually takes a sample of the fluid in order to determine a property of the fluid as it enters a centrifuge. The operator then manually controls parameters of the separation operation in order to produce a fluid having the desired properties. However, due to the variable properties of the fluids, the properties of the fluids may change rapidly. As such, in order to provide a fluid having the desired properties, the operator must take constant measurements and make corresponding adjustments in order to produce a fluid with the desired properties. Operation of separators in this manner results in an inefficient process and fluids that do not have the desired properties.

BRIEF SUMMARY OF THE INVENTION

According to one aspect of one or more embodiments of the present invention, a separation system includes a control unit, a first pump connected to the control unit, and a first valve in fluid communication with the first pump and connected to the control unit. Also, a first density meter in fluid communication with the first valve and connected to the control unit. The system further includes a separator in fluid communication with the density meter and connected to the control unit and a tank in fluid communication with the separator. The system also includes a second pump in fluid communication with the tank and connected to the control unit, as well as a second density meter in fluid communication with the second pump and connected to the control unit and a second valve in fluid communication with the second density meter and connected to the control unit.

According to another aspect of one or more embodiments of the present invention, a method of optimizing the density of a fluid includes selecting an optimized density parameter, determining a first density of a fluid, and removing a solids portion from the fluid based on the optimized density parameter. The method further includes determining a second density of the fluid, comparing the second density of the fluid to the optimized density parameter, and reprocessing the fluid based on the comparing the second density of the fluid to the optimized density parameter.

According to another aspect of one or more embodiments of the present invention, a method for optimizing the density of a fluid includes flowing a drilling fluid through a density meter, determining a density of the drilling fluid with the density meter, and flowing the drilling fluid though a separator. The method also includes removing a solid portion from the drilling fluid based on the density, flowing the drilling fluid through a second density meter, and determining a second density of the drilling fluid. The method further includes comparing the second density of the drilling fluid to an optimized density parameter and reprocessing the drilling fluid based on the comparing the second density of the drilling fluid to the optimized density parameter.

Other aspects of the present invention will be apparent from the following description and claims.

DETAILED DESCRIPTION OF THE INVENTION

One or more embodiments of the present invention are described in detail with reference to the accompanying figures. For consistency, like elements in the various figures are denoted by like reference numerals. In the following detailed description of the present invention, specific details are set forth in order to provide a thorough understanding of the present invention. In other instances, well-known features to one of ordinary skill in the art are not described to avoid obscuring the description of the present invention.

During drilling and production operations various types of separators may be used to control certain drilling and production fluid parameters such as, for example, density. Controlling density may be necessary and/or desirable in order to provide optimized drilling or production fluids during well operations. For example, in certain operations, a drilling operator may wish to introduce a drilling fluid, also referred to in the art as drilling mud, having a specific density in order to achieve or maintain wellbore stability. Drilling fluids having a specific density may also be used to control formation pressure, prevent damage to the wellbore, and seal formation.

Various types of drilling fluids may be used according to the methods and systems described herein. There are generally three types of drilling fluids that are commonly used, water-based fluids, non-aqueous fluids (i.e., oil-based fluids), and synthetic fluids. Depending on the type of operation and the type of fluid, the components of the fluids may vary. Examples of types of additives that may be used with drilling fluids include bentonite clay, barium sulfate, calcium carbonate, hematite, xanthan gum, guar gum, glycol, carbosymethycellulose, polyanionic cellulose, starch, deflocculants, acrylates, polyphosphates, lignosulfonates, and tannic acid, as well as other various additives that may be used to change the drilling fluid density, viscosity, and/or pH.

The density (i.e., mud weight) of drilling fluids is generally referred to in terms of pounds per gallon, (i.e., ppg or lb/gal). Depending on the type of well that is being drilled, the density of the drilling fluid may vary. Generally, drilling fluids around 9.0 ppg may be desirable. However, in certain operations, drilling fluids between 7.0 and 17.0 ppg, between 8.6 and 12.0 ppg, or between 9.1 and 9.8 ppg may be used. In still other embodiments, drilling fluids having a density less than 8.6 ppg or greater than 12.0 ppg may be used. The optimized density for a drilling fluid may depend on the type of well drilled, the formation type, the drill bit type, environmental issues, mud cake desirability, geological parameters, equipment parameters, well parameters, etc.

Embodiments of the present disclosure may provide methods and systems for controlling the density of fluids in hydrocarbon drilling and production operations. In certain embodiments, automated control units may be used to control various components in the system, thereby allowing a fluid in the system to be optimized prior to use or reuse. For example, control units may be used to control pumps, valves, meters, separators, tanks, agitation systems, and other system components as may be necessary to produce an optimized drilling fluid. Before describing the system in detail, individual components of the system are discussed below.

Figure 1:
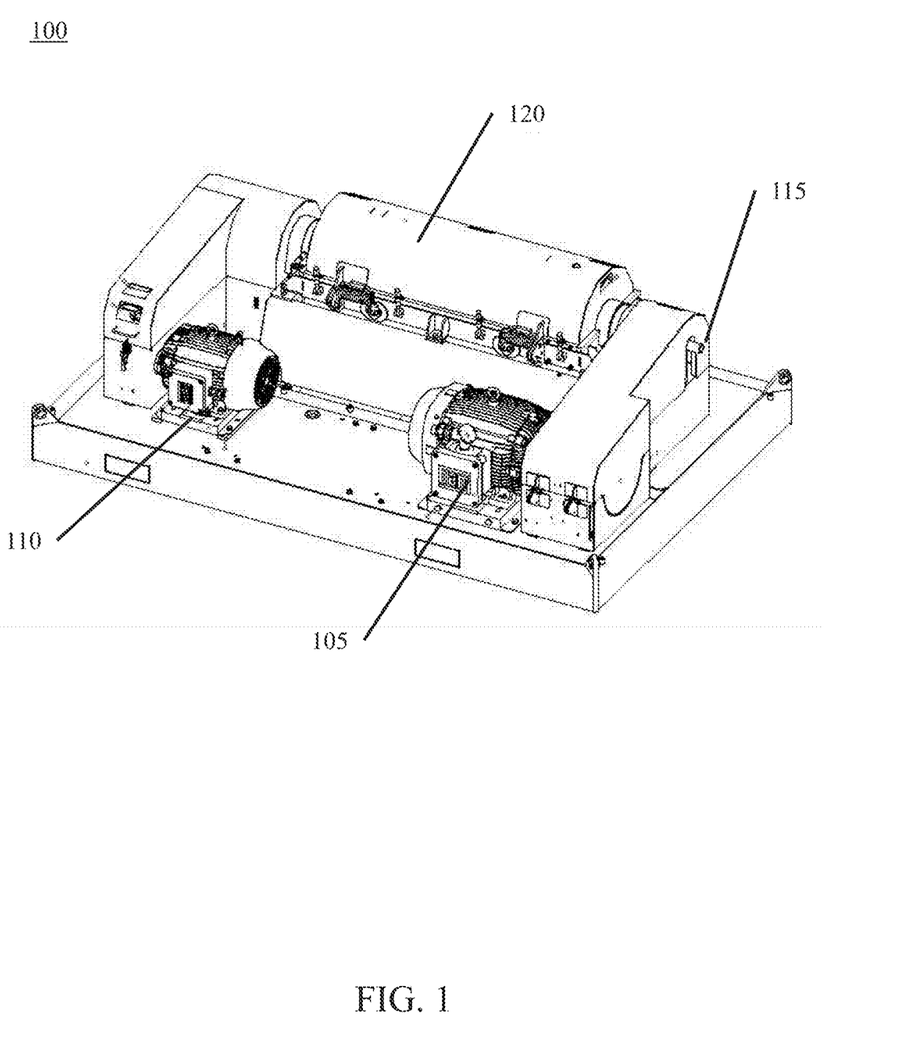
FIG. 1 shows a front perspective view of a separator according to one or more embodiments of the present invention.

Referring initially to FIG. 1, a front perspective view of a separator according to embodiments of the present invention is shown. In this embodiment, the separator 100 is a centrifuge, however, those of ordinary skill in the art will appreciate that in other embodiments other types of separators, such as those discussed above, may be used. Separator 100 includes a first motor 105 and a second motor 110. Separator 100 also includes a fluid inlet 115 and a separation chamber 120. During operation, fluid enters fluid inlet 115 and is processed in separation chamber 120, wherein a portion of a solid phase is separated from the liquid phase.

Motors 105 and 110 may vary in configuration and power, however, in this embodiment, first motor 105 is a 75 hp main drive motor and second motor 110 is a 25 hp secondary motor. In other embodiments, the motor configuration and power may vary. For example, first motor 105 may be a motor having a horse power between 15 and 100. Similarly, second motor 110 may be a motor having a horse power between 10 and 75. Those of ordinary skill in the art will appreciate that other types of separators, and specifically centrifuges, may be used according to embodiments disclosed herein. Other separators 100 may have one motor or more than two motors.

Figure 2:
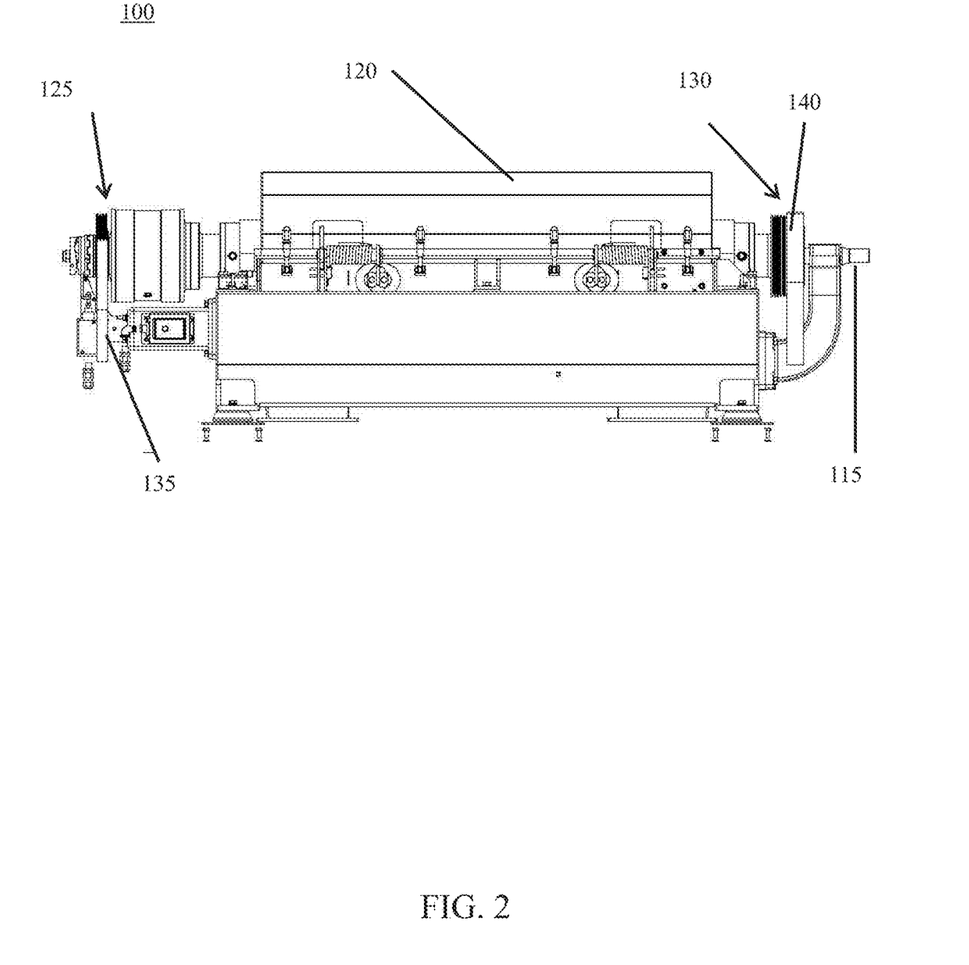
FIG. 2 shows a back view of a separator according to one or more embodiments of the present invention.

Referring to FIG. 2, a back view of a separator according to embodiments of the present invention is shown. In this embodiment, separator 100 is shown having a separation chamber 120 and a fluid inlet 115. Additionally, side sheaths (not independently shown) have been removed exposing belt drive systems 125 and 130 of motors (105 and 110 of FIG. 1, respectively). Belts 135 and 140 of motors (105 and 110 of FIG. 1, respectively), may be used to turn one or more conical drums (not independently shown).

Different types of separators 100 may be used according to embodiments disclosed herein. For example, in one embodiment, a relatively low-speed centrifuge may be used, wherein the separating point is between approximately 6 to 10 micrometers for low-density solids and between approximately 4 and 7 micrometers for high-density solids. In another embodiment, a medium-speed centrifuge may be used, wherein the separating point for solids is between approximately 5 and 7 micrometers. In still other embodiments, a high-speed centrifuge may be used, wherein the separating point for solids is between approximately 2 and 5 micrometers.

Figure 3:
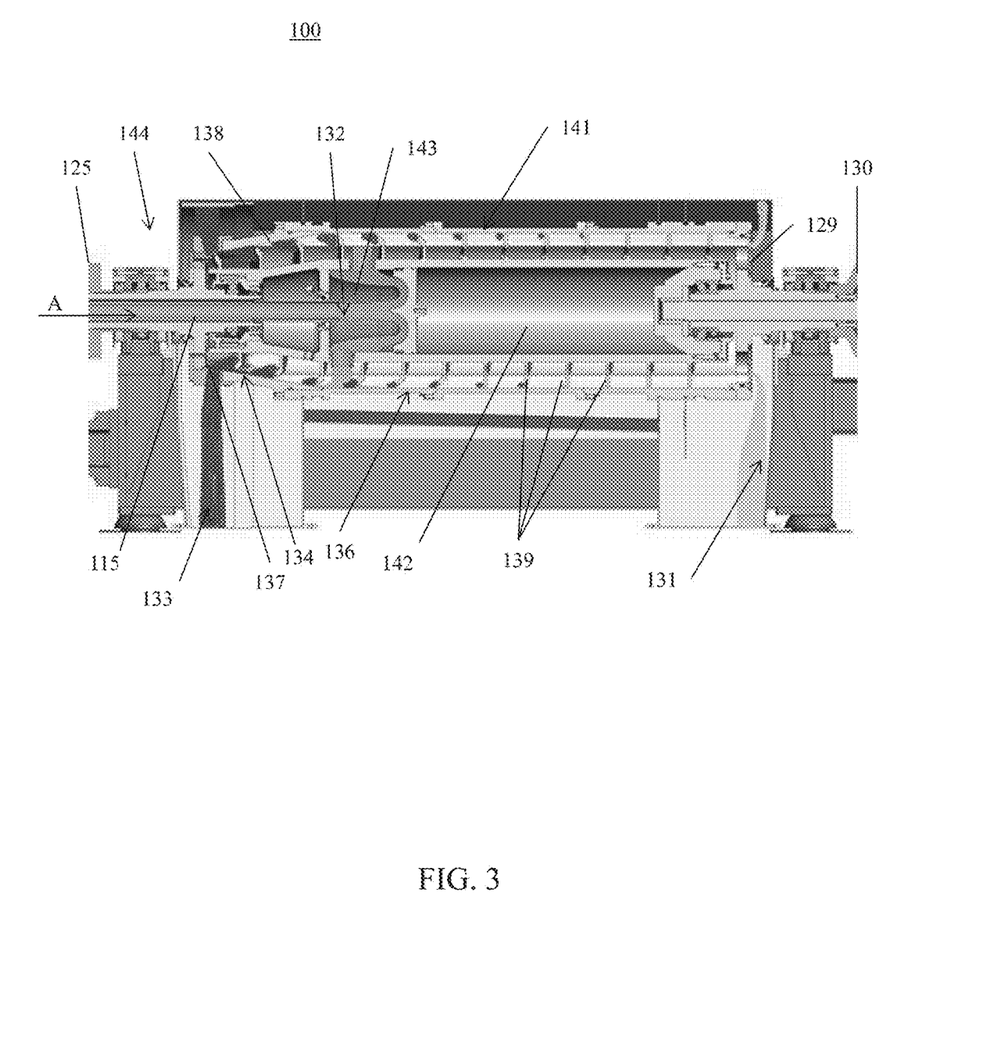
FIG. 3 shows a cross-sectional view of a separator according to one or more embodiments of the present invention.

Referring to FIG. 3, a cross-sectional view of a separator according to embodiments of the present invention is shown. In this embodiment, a separator 100 is shown having a bowl assembly 141 disposed around a conveyor 142. The bowl assembly 141 and/or conveyor 142 may be made from various materials include metals and metal alloys, plastics, and composites. For example, in one embodiment bowl assembly 141 and/or conveyor 142 may be made from stainless steel. Conveyor 142 further includes an accelerating chamber 143 disposed at a fluid inlet end 144 of separator 100.

A plurality of flights 139 may be disposed between bowl assembly 141 and conveyor 142, controlling a flow of fluid therethrough. Bowl assembly 141 further includes a conical 138 having one or more ejection ports 137 disposed thereon. Separator 100 further includes a belt drive systems 130 and 125, which are used to rotate bowl assembly 141 and conveyor 142, respectively.

During operation, a fluid 132 laden with solids material 133 or other particulate matter is flowed through fluid inlet 115 in direction A into separator 100. The bowl assembly 141 and/or the conveyor 142 are rotated at desired speeds. The fluid 132 enters accelerating chamber 143 and as the bowl assembly 141 and the conveyor 142 rotate, the fluids 132 move from accelerating chamber 143 into the area between bowl assembly 141 and conveyor 142. The differential speed between bowl assembly 141 and conveyor 142 causes solids 133 to accumulate along an inner wall 136 of bowl assembly 141. The separated solid material 133 is then moved up the bowl assembly 141 to an angled portion known in the art as a beach 134. The solid material 133 may then exit separator 100 and be collected for disposal or reuse. The separated fluid 131 flows in the opposite direction of solid material 133 and exits separator 100 for disposal or reuse.

Separator 100 may be configured to remove solids of a particular density by adjusting one or more parameters of separator 100. In one embodiment, the angle of flights 139 may be varied to control the separation of fluids 131 from solid material 133. In other embodiments, a pond depth may be controlled by adjusting dam plates 129. Pond depth refers to the fluid level between bowl assembly 141 and conveyor 142. In order to achieve a dryer solid portion 133, dam plates 129 may be rotated out, thereby increase pond depth, which will result in the drying solid portion. In another application, dam plates 129 may be rotated in, thereby decreasing pond depth resulting in a less dry solid portion 133.

Those of ordinary skill in the art will appreciate that the rotation rates of bowl assembly 141 and conveyor 142 may vary according to operational requirements. In one embodiment, bowl assembly 141 may rotate between 0 and 3000 revolutions per minutes (rpm). Conveyor 142 may rotate between 1 and 1750 rpm. In certain embodiments, bowl assembly 141 may rotate in the same direction as conveyor 142, while in other embodiments bowl assembly 141 and conveyor 142 may rotate in the same direction. In still other embodiments, either bowl assembly 141 or conveyor 142 may be relatively stationary, while the other component rotates.

While separator 100 illustrated in FIG. 3 shows a decanting centrifuge, those of ordinary skill in the art will appreciate that other types of separators 100, such as, for example, shakers or hydrocyclones may also be used to separate solid material 133 from fluids 131.

Referring to FIG. 4, a schematic cross-sectional view of a rotary pump according to embodiments of the present invention is shown. Different types of pumps 145 may be used according to embodiments of the present invention. One type of pump 145 that may be used is a rotary lobe pump 145, which is shown in three phases of operation in FIG. 4. Generally, rotary lobe pump 145 has a body 150 and two lobes 155.

Figures 4A, 4B:
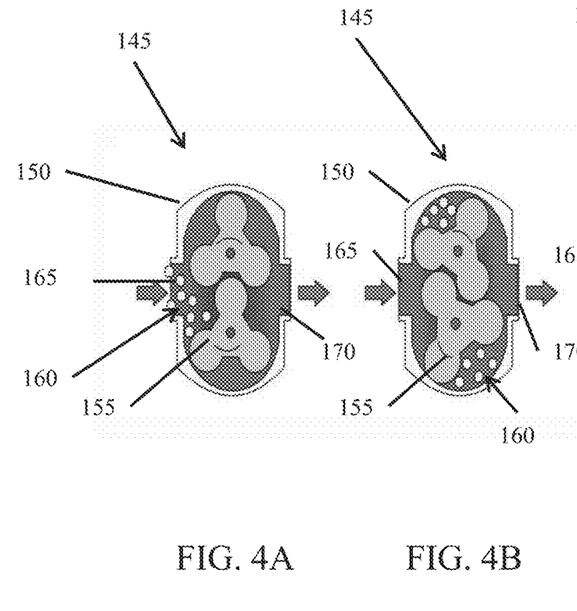
FIGS. 4A, 4B, and 4C show schematic cross-sectional views of a rotary pump according to one or more embodiments of the present invention.
Figure 4C:
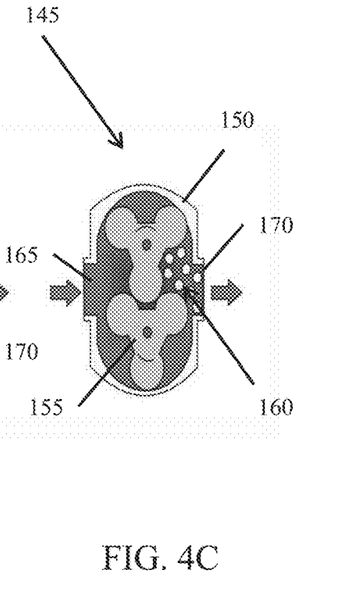

As shown in FIG. 4A, as lobes 155 rotate out of meshing, a fluid containing solids 160 is pulled into body 150 through inlet port 165. The fluid containing solids 160 travels around the interior of the body 150 in the pockets between the lobes 160 and the body 150 (FIG. 4B). Finally, as shown in FIG. 4C, the meshing of the lobes 155 forces the fluid containing solids 160 through an outlet port 170 under pressure.

In other embodiments, other types of pumps 145 may be used. In one embodiment, a centrifugal pump may be used. In a centrifugal pump, an impeller in combination with a shaped pump housing applies centrifugal force to discharge fluids from the pump 145. Examples of other pumps include general positive displacement pumps, duplex pumps, triplex pumps, jet pumps, etc. Those of ordinary skill in the art will appreciate that any type of pump used in hydrocarbon drilling and production operations may be used according to embodiments of the present invention.

Figure 5:
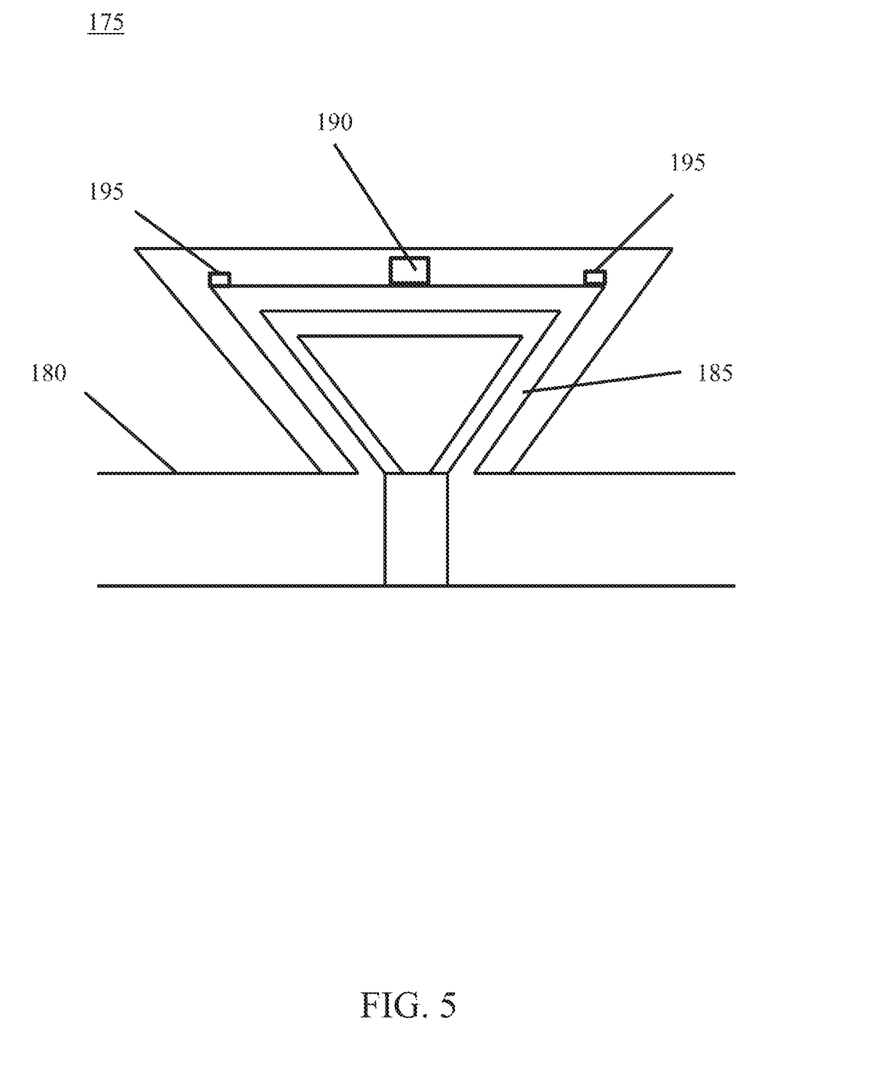
FIG. 5 shows a cross-sectional view of a density meter according to one or more embodiments of the present invention.

Referring to FIG. 5, a longitudinal cross-sectional view of a density meter according to embodiments of the present invention is shown. Embodiments of the present invention may use various types of measurement tools in order to measure properties of a fluid within the system. One type of meter that may be used is a density meter 175 or mass flow meter.

One type of density meter 175 that may be used is a Coriolis flow meter. In a Coriolis meter, a fluid traveling in a conduit 180 is passed into one of two tubes 185 (only one tube 185 is illustrated in cross-section). Tubes 185 may be U-shaped, horseshoe-shaped, or of different geometry, as will be appreciated by those of ordinary skill in the art. While the tubes 185 in this embodiment are illustrated as being curved, in other embodiments, the tubes 185 may be straight. As the fluid flows into tubes 185, the fluid is divided between the two tubes 185. When the fluid enters the tubes 185, the tubes 185 experience an oscillating excitation force that causes the tubes to vibrate at a fixed frequency. The vibration is induced in a direction that is perpendicular to the flow of the fluid.

During operation, an electromagnetic exciter 190 excites the tubes 185 in its first resonance frequency. When no mass is flowing tubes 185 oscillate symmetrically. When the fluid flows through tubes 185 the tubes 185 deform proportionately to the mass flow rate. The deformation may then be registered by two or more sensors 195 located at various locations on tubes 185. Because a phase shift occurs between the sensors 195, the mass flow rate may be derived from the phase shift difference. The density of the fluid may then be determined by the oscillation frequency of the tubes 185.

Figure 6:
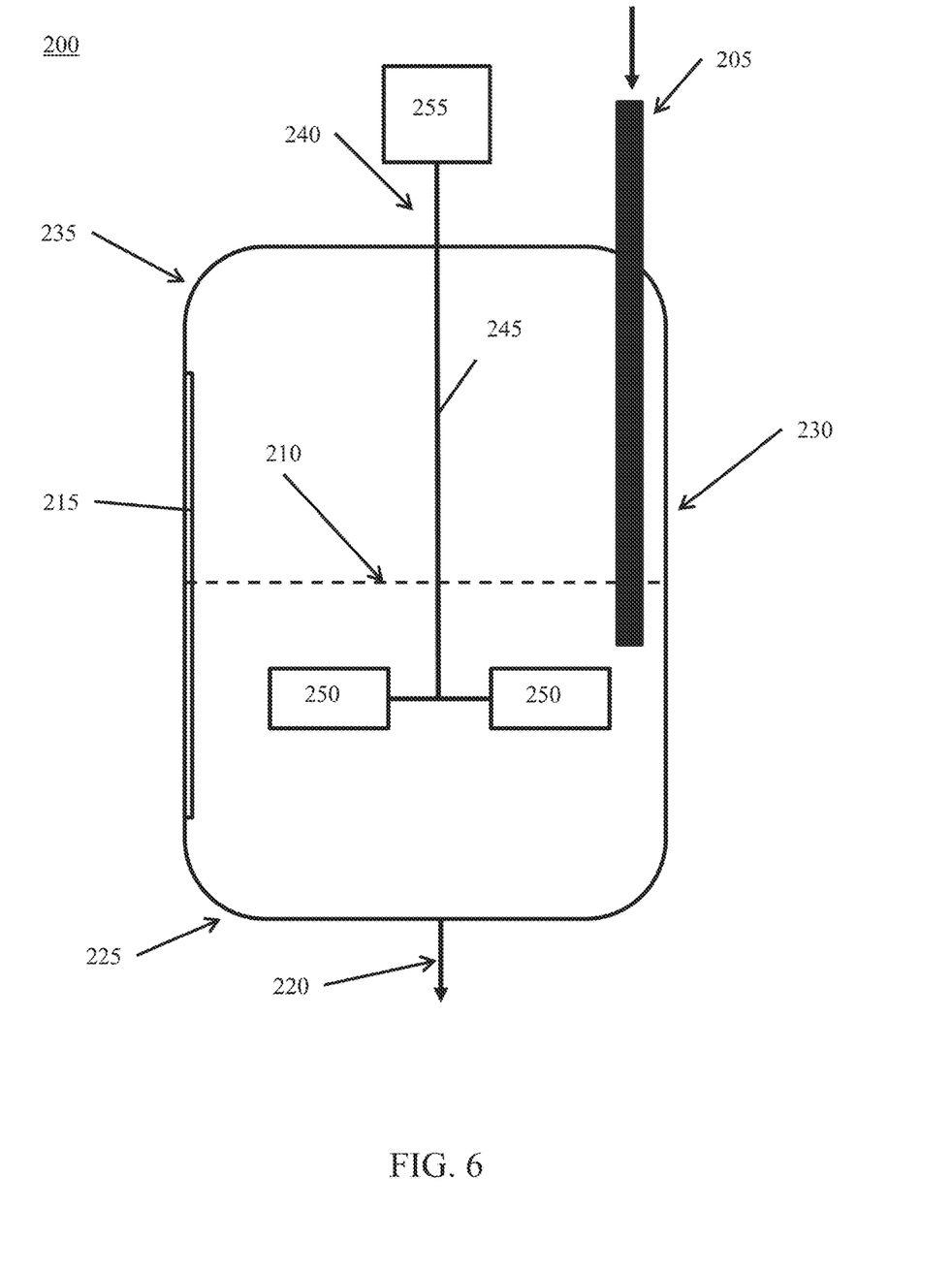
FIG. 6 shows a cross-sectional view of a tank according to one or more embodiments of the present invention.

Referring to FIG. 6, a side cross-sectional view of a tank according to embodiments of the present invention is shown. Tank 200 may be any type of tank that may store fluids used in hydrocarbon drilling and production operations. For example, tank 200 may be made from metals, such as stainless steel and stainless steel alloys, plastics, or composites. Tank 200 may have an inlet 205, such as an inlet pipe, that extends into tank 200 to a certain location. As illustrated, inlet 205 extends into tank 200 below a fluid level 210. Tank 200 may also have an outlet 220. In this embodiment, outlet 220 is illustrated at a basal location 225 of tank 200. However, in other embodiments, outlet 220 may be located along a side 230 of tank 200, or on the top 235 of tank 200. If the outlet 220 is located proximate the top 235 of tank 200, a separate outlet pipe (not shown) along with pumping apparatus (not shown) may be used to remove fluid from tank 200

Tank 200 may also include a fluid level sensor 215. As illustrated, fluid level sensor 215 is disposed on a side of tank 200, thereby allowing the fluid level 210 may be determined. In another embodiment, fluid level sensor 215 may include a sensor that floats on top of the fluid, thereby allowing the fluid level 210 to be determined. In embodiments where a fluid level sensor 215 is used, the fluid level sensor 215 may be connected to a control unit (not shown), so that the fluid level may be used in other aspects of the present invention. The fluid level sensor 215 may be connected to the control unit through either conventional wire-based systems or it may be connected wirelessly.

Tank 200 may also include an agitator 240. In this embodiment, agitator 240 is a paddle-style agitator 240 that include a drive shaft 245, with one or more paddles 250 disposed thereon. The drive shaft 245 is connected to a motor 255, thereby allowing the paddles to be moved within tank 200. The agitator 240 may be used to induce movement to the fluid within tank 200, thereby allowing fluids and solids to be mixed. Additionally, certain fluids may experience settling within tank 200. To prevent solids from settling out of the fluid, the agitator may be used move the solids within the fluid, thereby providing a substantially homogeneous fluid.

Agitator 240 may also be connected to the control unit, thereby allowing agitator 240 to be operated according to a provided schedule. For example, certain fluids may require frequent mixing, while other fluids may require intermittent mixing. In addition to controlling the timing of the mixing, control unit may control the speed of the mixing. In certain embodiments, properties of the fluid may be determined by agitator 240 and the control unit. For example, the torque required to turn drive shaft 245 may be supplied to the control unit, thereby allowing a viscosity and/or density to be calculated. As explained above, the agitator 240 may be connected to the control unit through either conventional wire-based systems or it may be connected wirelessly.

In addition to mechanical agitators 240, other types of agitators 240 may be used in various embodiments of the present disclosure. For example, movement may be imparted into tank 200 through hydraulic flow or pneumatic flow.

Figure 7:
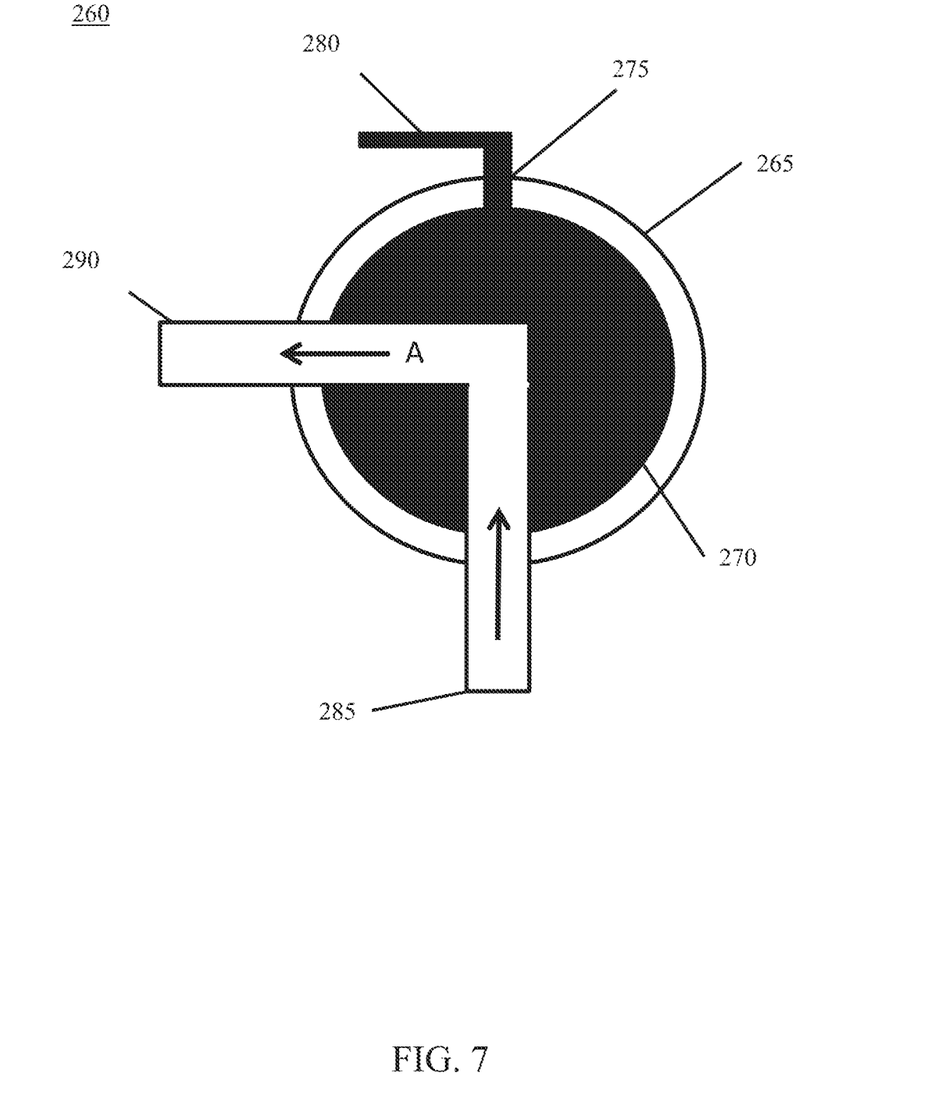
FIG. 7 shows a cross-sectional view of a valve according to one or more embodiments of the present invention.
Figure 8:
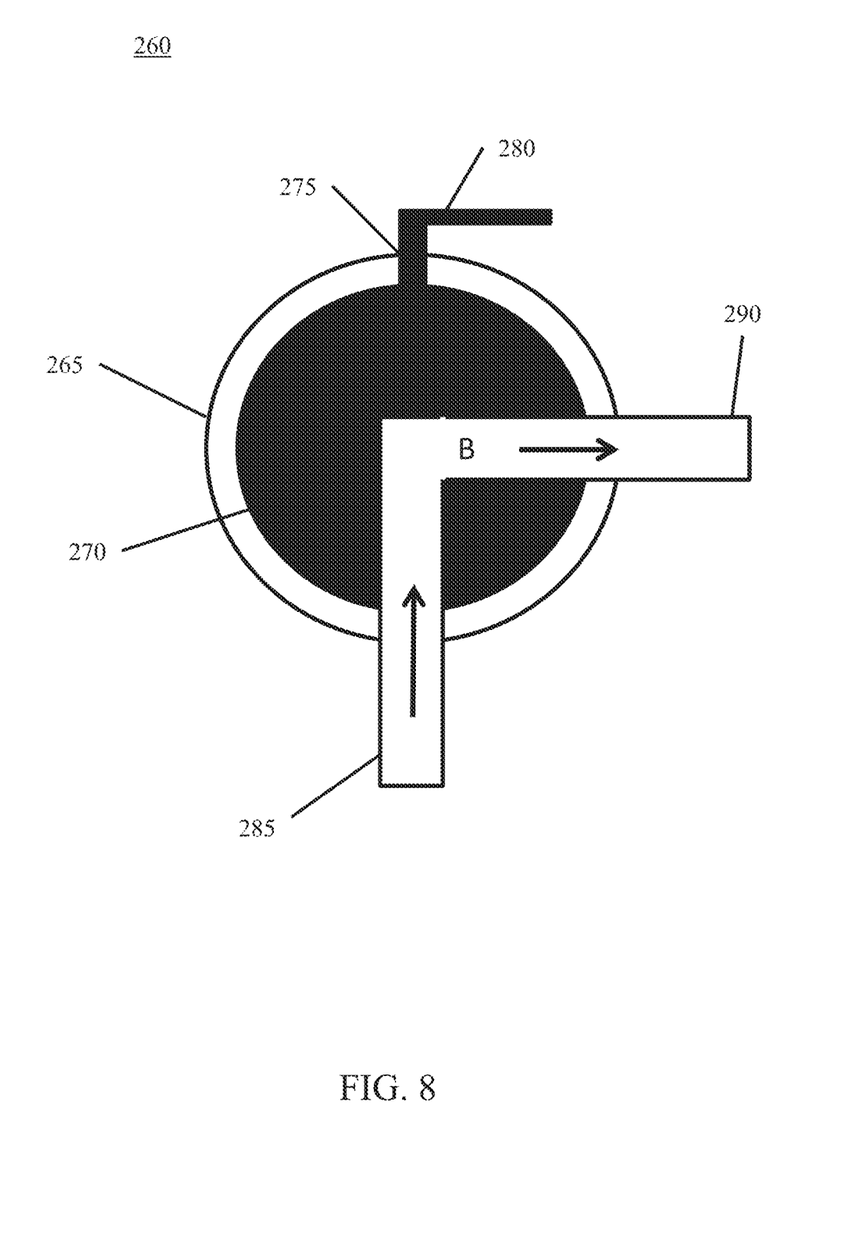
FIG. 8 shows a cross-sectional view of a valve according to one or more embodiments of the present invention.

Referring to FIGS. 7 and 8 together, side cross-sectional views of a three-way valve according to embodiments of the present invention is shown. A three-way valve 260 allows the flow of a fluid through a system to be routed in two different directions.

One type of three-way valve 260 is a ball valve. Ball valve 260 includes a body 265 and an inner disc 270 disposed within body 265. A seat (not illustrated) may be used to hold inner disc 270 within body 265 and to prevent fluid from flowing in an incorrect direction. Ball valve 260 may further include a stem 275 connected to inner disc 270, as well as a handle 280 for manual actuation of ball valve 260.

Referring specifically to FIG. 7, ball valve 260 may further include an inlet port 285 and an outlet port 290. During operation, a fluid may flow into ball valve 260 through inlet port 285. The fluid may continue to flow in direction A and exit ball valve 260 through outlet port 290. When the direction of the fluid within a system is rerouted, the handle 280 may be rotated into a different position, thereby turning inner disc 270 and changing the flow path of the fluid within ball valve 260. Referring specifically to FIG. 8, in s second position, the fluid may flow into ball valve 260 through inlet port 285. The fluid may continue to flow in direction B and exit ball valve 260 through outlet port 290.

In addition to ball valves 260, other types of valves 260 may be used in various embodiments of the present disclosure. In another embodiment, valves may include different types of hydraulic, pneumatic, manual, solenoid, and or motor driven valves.

Those of ordinary skill in the art will also appreciate that valves 260 may actuate between different positions manually and/or automatically. In one embodiment, valves 260 may be connected to a control unit (not shown), such that actuation of the valve may be automatically controlled. The actuation of valves 260 may be in response to a calculated fluid parameter, such as a density, as explained above. Thus, valve 260 may be used to change the fluid flow in a system, thereby allowing an optimized density for a fluid to be provided. Valves 260 may be connected to the control unit through either conventional wire-based systems or may be connected wirelessly.

Figure 9:
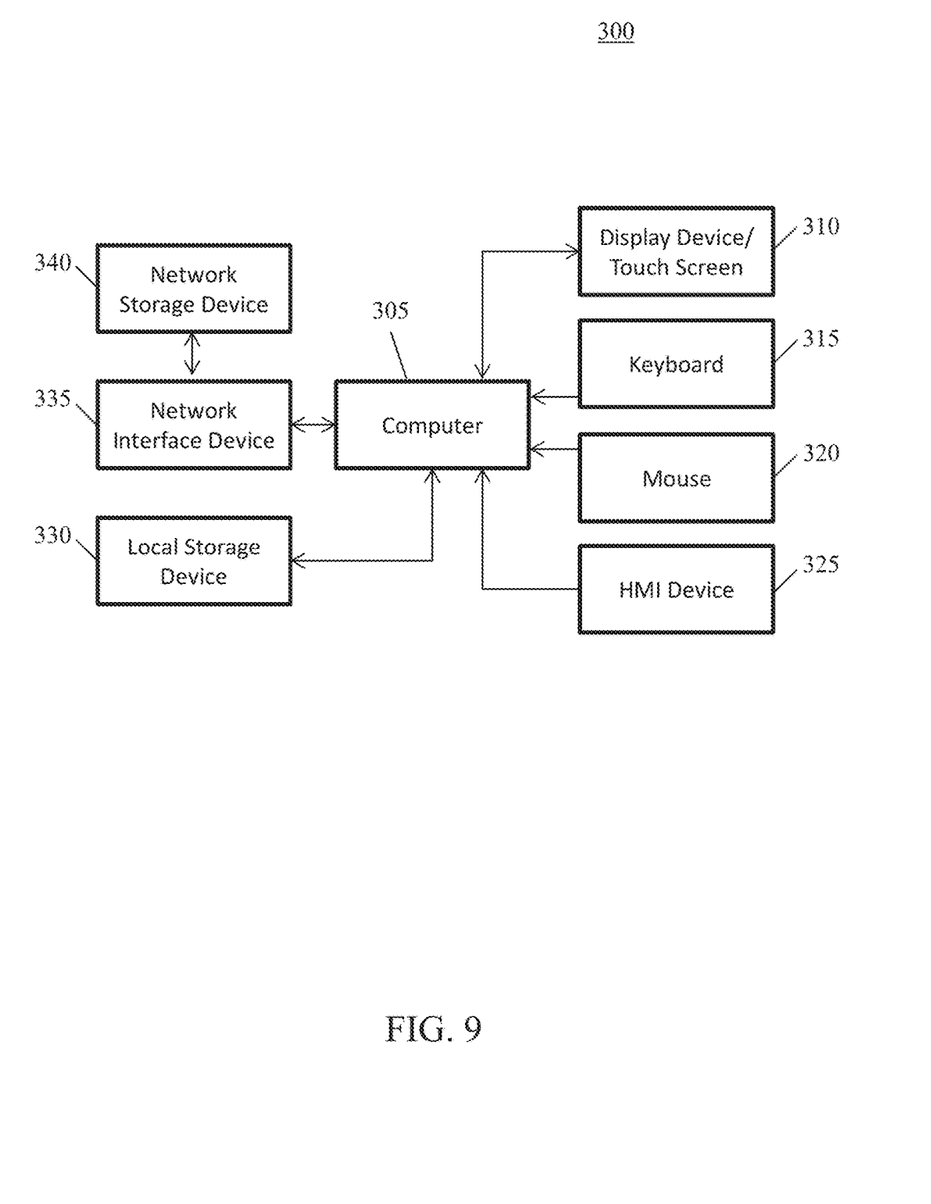
FIG. 9 shows a schematic representation of a control unit according to one or more embodiments of the present invention.

Referring to FIG. 9, a schematic representation of a control unit according to embodiments of the present disclosure is shown. The control unit may generally be a computing system 300 in accordance with one or more embodiments of the present invention. Computing system 300 may include one or more computers 305 that each includes one or more printed circuit boards (not shown) or flex circuits (not shown) on which one or more processors (not shown) and system memory (not shown) may be disposed. Each of the one or more processors (not shown) may be a single-core processor (not shown) or a multi-core processor (not shown). Multi-core processors (not shown) typically include a plurality of processor cores (not shown) disposed on the same physical die or a plurality of processor cores (not shown) disposed on multiple die that are disposed in the same mechanical package. Computing system 300 may include one or more input/output devices such as, for example, a display device 310, keyboard 315, mouse 320, and/or any other human-machine interface device 325. The one or more input/output devices may be integrated into computer 305. Display device 310 may be a touch screen that includes a touch sensor (not shown) configured to sense touch. A touch screen enables a user to control various aspects of computing system 300 by touch or gestures. For example, a user may interact directly with objects depicted on display device 310 by touch or gestures that are sensed by the touch sensor and treated as input by computer 305.

Computing system 300 may include one or more local storage devices 330. Local storage device 330 may be a solid-state memory device, a solid-state memory device array, a hard disk drive, a hard disk drive array, or any other non-transitory computer readable medium. Local storage device 330 may be integrated into computer 305. Computing system 300 may include one or more network interface devices 340 that provide a network interface to computer 305. The network interface may be Ethernet, Wi-Fi, Bluetooth, WiMAX, Fibre Channel, or any other network interface suitable to facilitate networked communications. Computing system 300 may include one or more network-attached storage devices 340 in addition to, or instead of, one or more local storage devices 330. Network-attached storage device 340 may be a solid-state memory device, a solid-state memory device array, a hard disk drive, a hard disk drive array, or any other non-transitory computer readable medium. Network-attached storage device 350 may not be collocated with computer 305 and may be accessible to computer 305 via one or more network interfaces provided by one or more network interface devices 335. One of ordinary skill in the art will recognize that computer 305 may be a server, a workstation, a desktop, a laptop, a netbook, a tablet, a smartphone, a mobile device, and/or any other type of computing system in accordance with one or more embodiments of the present invention.

Control unit 300 may be connected to various other components within a fluid density optimization system, as disclosed above. Examples of components that may be connected to and/or controlled at least in part by control unit 300 include valves, meter, sensors, tanks, separators, pumps, and components thereof. The various components may be connected to the control unit through either conventional wire-based systems or they may be connected wirelessly. Those of ordinary skill in the art will appreciate that embodiments of the present invention may include one or more control units 300 and the control units 30, in addition to the individual components described above, may further include various additional components not explicitly recited herein.

Figure 10:
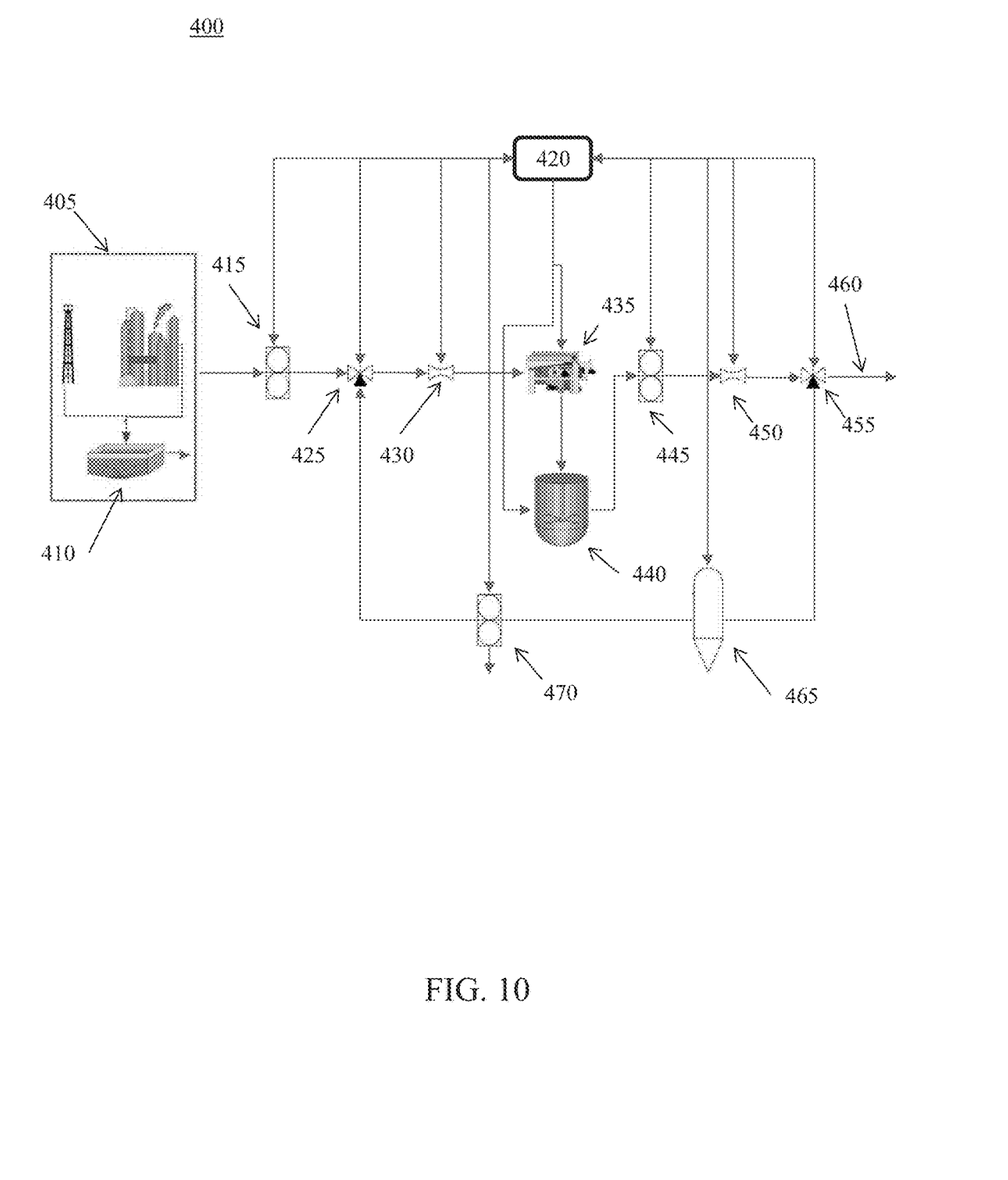
FIG. 10 shows a schematic representation of a fluid density optimization system according to one or more embodiments of the present invention.

Referring to FIG. 10, a schematic representation of a fluid density optimization system according to embodiments of the present invention is shown. Those of skill in the art will appreciate that in certain embodiments not all components illustrated in FIG. 10 are required in a fluid density optimization system. Additionally, in certain fluid density optimization systems, additional components may be used to further optimize a fluid.

Fluids that may be processed using system 400 may originate from a number of difference places such as, for example, drilling sites and production wells 405. The fluids may have been used in previous drilling and/or production operations and, as such, may contain undesirable solids. Undesirable solids may include drill cuttings, formation fragments, fluid additives, and the like. Initially, the fluid may be processed through course separators (not shown) such as shale shakers, dryers, low-speed centrifuges, screens, and other mechanical separators. While the course separators may remove large solid material, course separators are generally not effective at removing fine materials, such as solids less than approximately 10 micrometers. Course separation may occur prior to storage or, in certain embodiments, the fluid may be sent to a storage system such as those described below.

At certain work sites, the fluids may be held in a mud tank 410. Mud tank 410 may include any type of tank that is capable of holding a drilling or production fluid. Examples of tanks that may be used as mud tanks 410 are described above with respect to FIG. 6. In other embodiments, mud tank 410 may be a lined or unlined pit at a drilling location. After the fluid is returned from a work site, the fluid may undergo course separation or be transferred directly to mud tank 410. In certain operations, prior to introduction into system 400, but after being stored in mud tank 410, the fluid may undergo course separation or some other form of separation. Additionally, in certain operations, the fluid in mud tank 410 may be agitated prior to introduction into system 400, thereby promoting a fluid having a more homogeneous density.

Fluid is initially pumped into system 400 through first pump 415. Pump 415 may be any type of pump 415 discussed with respect to FIG. 4. In one embodiment, pump 415 may be a rotary lobe pump. Pump 415 is in fluid communication with a fluid source, such as mud tank 410. As the fluid is pumped through pump 415, a control unit 420 may monitor the flow of fluid therethrough. In addition to monitoring the flow rate of the fluid through pump 415, control unit 420 may be used to control a pump parameter, such as the speed of pump 415, thereby controlling the flow rate of fluid into system 400. The speed of pump 415 may be controlled by controlling a motor (not shown independently) speed. Flow rate of the fluid into system 400 may vary based on the requirements of the operation; however, those of ordinary skill in the art will appreciate that the inflow rate may vary between approximately 30 gallons per minute and approximately 300 gallons per minute. In still other embodiments, the inflow rate may vary between approximately 30 gallons per minutes and approximately 500 gallons per minute.

As pump 415 continues to bring fluid into system 400, the fluid may flow through a valve 425 in fluid communication with pump 415. The valve 425 may be any type of valve discussed with respect to FIGS. 7 and 8. In this embodiment, valve 425 is a three-way valve. In addition to being in fluid communication with pump 415, valve 425 is connected to control unit 420. Control unit 420 may control the actuation of valve 425, thereby determining whether to allow fluid further into system 400 from pump 415 or to recirculate fluid already within system 400. Control unit 420 may control valve 425 through mechanized or motorized actuation or through the use of solenoid valves or other electrically controlled valves. In certain embodiments, valve 425 may be a metering valve. Thus, valve 425 may be used to provide full pressure in one direction, while allowing partial flow from a second direction. In such an embodiment, a partial flow of recirculated fluid already within system 400 may supplement the flow from pump 415. In still other embodiments, rather than one valve, two or more separate valves may be used to control the fluid flow through system 400. In such an embodiment, a first valve may be actuated into an open or closed position, thereby controlling the flow of fluid from pump 415, while a second valve may be actuated into an open or closed position, thereby controlling the flow of fluid already within system 400. In such an embodiment, control unit 420 may monitor and control both valves substantially simultaneously, thereby allowing full flow from either direction, allowing full flow from one direction and partial flow from a second direction, or allowing partial flow from both directions.

After the fluid passes through valve 425, the fluid may pass through a meter 430. Meter 430 may be used to measure fluid parameters such as density, temperature, and flow rate. The fluid parameters may be acquired through multiple inline sensors or a single integrated sensor. An example of a density meter may include a Coriolis meter, as discussed with respect to FIG. 5. In addition to density meter 430 being fluidly connected to valve 425, meter 430 may also be connected to control unit 420. Meter 430 may take substantially continuous measurements of, for example, the density of the fluid flowing therethrough or, in certain embodiments, may take measurements in predefined time increments. Examples of time increments that may be used include every 15 seconds, every 30 seconds, every minute, or a different time increment that an operator may determine is sufficient to produce an optimized fluid. The density measurements may then be communicated to control unit 420 and, based on the density measurement, control unit 420 may adjust a parameter of system 400. Examples of system parameters that control unit 420 may adjust based on such density measurements are described in detail below.

After an initial density of the fluid is determined, the fluid flows into a separator 435. As described above, various types of separators 435 may be used; however, in this embodiment separator 435 includes a centrifuge. In addition to separator 435 being fluidly connected to density meter 430, separator 435 may be connected to control unit 420. Based on the measured density of the fluid, an operating parameter of separator 435 may be adjusted. Examples of separator operating parameters include a motor speed, such as a main drive speed and/or a back drive speed, direction control, pump speed, a flow rate, a separation gradient, etc. In separator 435 a certain percentage of solids may be removed from the fluid. The removed solids may be transferred to a solids holding tank (not shown) for further reintroduction into system 400 or for discard. The fluid that passes through centrifuge may contain residual solids; however, the density of the effluent from separator 435 may be less than the density of the fluid introduced into separator 435. In the case of a fluid that is recycled through system 400, the density change may be minimal and in some cases the density of the effluent may be substantially the same as the introduced fluid.

The effluent from separator 435 may then be transferred to a tank 440 in fluid communication with separator 435. Tank 440 may be any type of tank discussed above with respect to FIG. 6. In some embodiments, tank 440 may also be connected to control unit 420. Control unit 420 may receive measurement data from tank 440 such as fluid level, temperature, and in the case of tanks 440 with agitators, agitator control parameters. Examples of agitator control parameters may include, for example, motor speed, drive shaft torque, paddle speed, etc. Tank 440 may be used to store separator 435 effluent for a desired time before removing the fluid therefrom. In certain embodiments, the fluid may be stored until a certain volume of fluid is available for transfer. In other embodiments, the fluid may be substantially continuously removed from tank 440. In still other embodiments, tank 440 may be removed from system 400, thereby allowing the fluid to bypass tank 440 and flow to other components of system 400.

The fluid in tank 440 may be transferred from tank 440 through use of a second pump 445. As with pump 425, second pump 445 may be any type of pump, such as those described with respect to FIG. 4. Second pump 445 may be fluidly connected to tank 440 or, in certain embodiments, may be fluidly connected directly to separator 435. In still other embodiments, second pump 445 may be selectively in fluid communication with either separator 435 or tank 440 through use of an intermediary valve (not shown). In such an embodiment, an operator may selectively actuate intermediary valve, thereby selecting pumping fluid from either separator 435 or tank 440. Second pump 445 may also be connected to control unit 420. Control unit 420 may be used to control various pump parameters such as, for example, pump speed. Control system 420 may also monitor the flow rate through second pump 445, thereby allowing control unit 420 to adjust the speed of second pump 445.

Second pump 445 may provide a flow of fluid thorough a second meter 450. Second meter 450 may be used to measure fluid parameters such as density, temperature, and flow rate. The fluid parameters may be acquired through multiple inline sensors or a single integrated sensor. Second meter 450 may also be any type of density meter, such as a Coriolis meter, as discussed with respect to FIG. 5. In addition to second meter 450 being fluidly connected to second pump 445, second meter 450 may also be connected to control unit 420. Second meter 450 may take substantially continuous measurements of the density of the fluid flowing therethrough or, in certain embodiments, may take measurements in predefined time increments. Examples of time increments that may be used include every 15 seconds, every 30 seconds, every minute, or a different time increment that an operator may determine is sufficient to produce an optimized fluid. The density measurements may then be communicated to control unit 420 and based on the density measurement, control unit 420 may adjust a parameter of system 400. Examples of system parameters that control unit 420 may adjust based on such density measurements are described in detail below.

After the fluid flows through second meter 450, the fluid may flow through a second valve 455. Second valve 455 may be any type of valve discussed with respect to FIGS. 7 and 8. In this embodiment, second valve 455 is a three-way valve. In addition to being in fluid communication with pump second density meter 450, second valve 455 is connected to control unit 420. Control unit 420 may control the actuation of second valve 455, thereby determining whether to allow fluid further through system 400 or to recirculate fluid already within system 400. Control unit 420 may control second valve 455 through mechanized or motorized actuation or through the use of solenoid valves or other electrically controlled valves.

If control unit 420 determines, based on the density measurements from second density meter 450 that the fluid is optimized, second valve 455 may be opened, thereby allowing the optimized fluid to flow out of system 400 through an outlet line 460 for use in a drilling or production operation. Thus, system 400 may be fluidly connected to an active fluid system through outlet line 460. If control unit 420 determines, based on the density measurements from second density meter 450, that the fluid is not optimized or otherwise does not have the desired density, second valve 455 may be closed, thereby allowing the non-optimized fluid to flow back into system 400. The flow of non-optimized fluid back into system 400 is referred to herein as recirculation.

If control unit 420 determines that the fluid is non-optimized, valve 455 may be actuated, thereby directing the fluid into a second tank 465. Second tank 465 may be any type of tank discussed above with respect to FIG. 6. In some embodiments, second tank 465 may also be connected to control unit 420. Control unit 420 may receive measurement data from second tank 465 such as fluid level, temperature, and in the case of second tanks 465 with agitators, agitator control parameters. Examples of agitator control parameters may include, for example, motor speed, drive shaft torque, paddle speed, etc. Second tank 465 may be used to store non-optimized fluid during recirculation through system 400. In certain embodiments, the fluid may be stored until a certain volume of fluid is available for transfer. In other embodiments, the fluid may be substantially continuously removed from second tank 465. In still other embodiments, second tank 465 may be removed from system 400, thereby allowing the fluid to bypass second tank 465 and flow to other components of system 400.

During recirculation of non-optimized fluid through system 400, control unit 420 or an operator may determine that rather than introduce new fluid into system 400, non-optimized fluid should be used. In such a situation, control unit 420 may actuate a third pump 470. As with pump 425 and second pump 445, third pump 470 may be any type of pump, such as those described with respect to FIG. 4. Third pump 470 may be fluidly connected to second tank 465 or, in certain embodiments, may be fluidly connected directly to second valve 455. Third pump 470 may also be connected to control unit 420. Control unit 420 may be used to control various pump parameters such as, for example, pump speed. Control system 420 may also monitor the flow rate through third pump 470, thereby allowing control unit 420 to adjust the speed of third pump 470.

During recirculation, control unit 420 may also actuate valve 425. Once valve 425 is in a recirculation position, fluid flow is allowed from third pump 470. The recirculation may continue until the fluid is optimized or until the control unit 420 determines that enough of the non-optimized fluid has been used. When control unit 420 determines to stop recirculation, control unit 420 may actuate valve 425 into a position to allow new fluid to enter system 400.

As discussed above, control unit may be used to control various system parameters. Examples of system parameters include fluid density, flow rate, valve actuation, separator parameters, density meter parameters, tank parameters, agitator parameters, and the like. Thus, an operator may supply a desired optimized fluid density or density range to control unit 420 and control unit 420 may substantially continuously adjust system parameters until the fluid is optimized.

Control unit 420, as well as various other components of system 400, may be connected to one or more variable frequency drives (not independently illustrated). The variable frequency drives may be used to control various aspects of system 400 including, for example, pumps, valves, meters, tanks, and separators. In addition to the automated aspects of system 400, through control unit 420, manual actuation of valves, separator controls, tank controls, or measurements may also be used to supplement the automated aspects.

In addition to the system described above, the present disclosure may provide methods for optimizing the density of a fluid. The method may initially include selecting an optimized density parameter. The optimized density parameter may include a specific density valve. In one embodiment, the density parameter may include a range between about 7.0 ppg and about 17.0 ppg. In another embodiment the density parameter may include a range between about 8.6 ppg and about 12.0 ppg. In another embodiment, the optimized density parameter may include a range between about 9.1 ppg and about 9.8 ppg. In still another embodiment, the optimized density parameter may include a density value of about 9.0.

After the density parameter is selected, a first density of a fluid is determined. The first density may be determined by flowing the fluid through a density meter and communicating the density to a control unit. After the first density is determined, a solids portion may be removed from the fluid based on the optimized density parameter. To remove the solids phase the fluid may be flowed through a separator. The separator may be used to remove at least a portion of a solids phase from the fluid. The solids may include entrained drilling waste and/or drilling fluid or production fluid additives. The portion of solids phase removed may vary based on the optimized density parameter. As such, various separator parameters may be adjusted by, for example, a control unit, as described above.

After removing at least a portion of the solids phase, a second density of the fluid is determined. The second density may be determined by flowing the fluid through a density meter and communicating the density to a control unit. After determining the second density of the fluid, the second density measurement is compared to the optimized density parameter and based on the results, the fluid may either be directed to an active system or reprocessed. For example, in one embodiment the optimized density parameter may include a density value of 9.0 ppg. The second density measurement may return a value of 9.2 ppg. The control unit may thus determine that the fluid does not have an optimized fluid density and prevent the fluid from flowing to an active system. In such a situation, the fluid may be redirected through system for reprocessing by the separator to remove additional solids. The recirculation of the fluid may continue until the fluid is determined to be optimized.

In still another embodiment, the optimized density parameter may include a density value of 9.0 ppg. The second density measurement may return a value of 8.6. The control unit may thus determine that the fluid does not have an optimized fluid density and thereby prevent the fluid from flowing to an active system. In such a situation, the fluid may be transferred to a holding tank and reintroduced into the system in order to thin new incoming fluid. Alternatively, additives may be combined with the non-optimized fluid until the fluid has an optimized density, at which point the fluid may be introduced into an active system.

In still another embodiment, a second optimized density parameter may be selected and the fluid may be reprocessed until a comparison of the second density of the fluid to the second optimized density parameter defines the fluid as having an optimized density. Such a situation may occur when a driller or producer requests a change to the density of the fluid, and the optimized density parameter may be changed substantially in real time. Thus, rather than produce full batches of fluid with outdated densities, the density may be adjusted, and the fluid recirculated in order to achieve an optimized density fluid based on the second optimized density parameter.

Embodiments of the present disclosure may also provide additional methods for optimizing the density of a fluid. In one embodiment a drilling fluid may be flowed through a density meter. The density meter may be used to determine the density of a drilling fluid. After the density of the drilling fluid is determined, the drilling fluid may be flowed through a separator. The separator may be used to remove a solid portion from the drilling fluid based on the measured density. After the solid portion is removed, the drilling fluid may be flowed through a second density meter. The second density meter may be used to determine a second density of the drilling fluid.

After the second density of the drilling fluid is determined, the second density of the drilling fluid may be compared to an optimized density parameter. After comparing the second density of the drilling fluid to the optimized density parameter, the drilling fluid may be reprocessed if the second density of the drilling fluid does not adequately meet the provisions of the optimized density parameter.

Such methods may also use valves, wherein the valves may be selectively opened and closed based on the comparing the second density of the drilling fluid to the optimized density parameter. In such a situation, one or more valves may be opened and/or closed in order to add fluid to the system, remove optimized fluid from the system, or recirculate non-optimized fluid within the system. When adding fluid to the system, recirculated non-optimized fluid may also be added. Thus, a combination of new fluid and recirculated fluid may be processed by system.

Additionally, such methods may remove a volume of solids from the fluid based on the optimized density parameter. For example, if the optimized density parameter is 9.0 ppg, and the fluid introduced to the separator is 9.1 ppg, the speed of the separator may be modified and/or the flow rate of fluid through separator may be modified in order to achieve a separator effluent having the optimized density valve.

Advantageously, embodiments of the present invention may provide automated systems for processing drilling and/or production fluids.

Advantageously, embodiments of the present invention may provide automated systems for processing drilling and/or production fluids having optimized density values.

Advantageously, embodiments of the present invention may provide systems for recirculating drilling and/or production fluid until the fluid has an optimized density value.

Advantageously, embodiments of the present invention may provide for on-the-fly adjustment of optimized fluid density parameters.

Advantageously, embodiments of the present disclosure may provide systems and methods for more efficiently processing drilling and production fluids.

While the present invention has been described with respect to the above-noted embodiments, those skilled in the art, having the benefit of this disclosure, will recognize that other embodiments may be devised that are within the scope of the invention as disclosed herein. Accordingly, the scope of the invention should be limited only by the appended claims.

What is claimed is:

1. A method for optimizing the density of a fluid, the method comprising:
   flowing a drilling fluid through a density meter;
   determining a density of the drilling fluid with the density meter;
   flowing the drilling fluid through a separator;
   processing the drilling fluid in the separator;
   removing a solid portion from the drilling fluid based on the density;
   flowing the drilling fluid through a second density meter;
   determining a second density of the drilling fluid;
   comparing the second density of the drilling fluid to an optimized density parameter; and
   reprocessing the drilling fluid in the separator based on the comparing the second density of the drilling fluid to the optimized density parameter.

2. The method of claim 1, further comprising flowing the drilling fluid through a valve, wherein the valve selectively opens based on the comparing the second density of the drilling fluid to the optimized density parameter.

3. The method of claim 1, wherein a volume of solids removed from drilling fluid is based on the optimized density parameter.

4. The method of claim 1, wherein the optimized density parameter comprises a range between 7.0 ppg and 17.0 ppg.

5. The method of claim 1, wherein the optimized density parameter comprises a range between 9.1 ppg and 9.8 ppg.

6. The method of claim 1, wherein the optimized density parameter is about 9.0 ppg.

7. The method of claim 1, further comprising adding additional solids to the fluid after removing the solids portion from the fluid.

8. The method of claim 1, further comprising selecting a second optimized density parameter and reprocessing the fluid based on the comparing the second density of the fluid to the second optimized density parameter.

9. A method for optimizing density of a drilling fluid, the method comprising:
selecting an optimized density parameter;
flowing the drilling fluid through a first pump;
passing the drilling fluid though a first density meter;
determining a density of the drilling fluid passing through the first density meter;
flowing the drilling fluid though a separator;
processing the drilling fluid in the separator;
removing a solid portion from the drilling fluid based on the optimized density parameter;
flowing the drilling fluid from the separator into a tank;
passing the drilling fluid through a second density meter;
determining a second density of the drilling fluid passing through the second density meter;
comparing the second density of the drilling fluid to the optimized density parameter; and
reprocessing the drilling fluid in the separator based on the comparing the second density of the drilling fluid to the optimized density parameter.

10. The method of claim 9, wherein the separator comprises a centrifuge.

11. The method of claim 9, further comprising:
agitating the drilling fluid in the tank.

12. The method of claim 9, wherein the first pump comprises a rotary lobe pump.

13. The method of claim 9, further comprising:
controlling the flow of drilling fluid with a control unit.

14. The method of claim 13, wherein the control unit comprises instructions to control the density of the drilling fluid by controlling a property of at least one of the first pump and the separator.

15. The method of claim 13, further comprising:
passing the drilling fluid through a first valve disposed between the first pump and the separator.

16. The method of claim 15, further comprising:
passing the drilling fluid through a second valve disposed between in the separator and the tank.

17. The method of claim 16, wherein the first valve and the second valve are connected to the control unit.

18. The method of claim 17, wherein the control unit comprises instructions to control the density of the drilling fluid by controlling a property of at least one of the first pump, the first valve, the second valve, the separator, and the tank.

19. The method of claim 18, further comprising:
modifying the instructions in the control unit to adjust the optimized density parameter.

20. The method of claim 9, wherein the optimized density parameter comprises a range between 7.0 ppg and 17.0 ppg.

21. The method of claim 9, wherein the optimized density parameter comprises a range between 9.1 ppg and 9.8 ppg.

22. The method of claim 9, wherein the optimized density parameter is about 9.0 ppg.

23. The method of claim 9, further comprising adding additional solids to the drilling fluid after removing the solids portion from the drilling fluid.

24. The method of claim 9, further comprising selecting a second optimized density parameter and reprocessing the drilling fluid based on the comparing the second density of the drilling fluid to the second optimized density parameter.

\* \* \* \* \*